(12) United States Patent
Vasiliev et al.

(10) Patent No.: US 7,593,768 B1
(45) Date of Patent: Sep. 22, 2009

(54) DETECTION OF SMOOTH MUSCLE MOTOR ACTIVITY

(75) Inventors: Vladislav Vasiliev, Moscow (RU); Yokov Azarov, Moscow (RU); Olga Notov, Haifa (IL)

(73) Assignees: Medisense Technologies (International) Ltd., Gibraltar (ES); Medisense P.E. Technologies Ltd., Ra'Ananna (IL)

(*) Notice: Subject to any disclaimer, the term of this patent is extended or adjusted under 35 U.S.C. 154(b) by 0 days.

(21) Appl. No.: 09/959,097

(22) PCT Filed: Apr. 11, 2000

(86) PCT No.: PCT/IL00/00215

§ 371 (c)(1), (2), (4) Date: May 22, 2002

(87) PCT Pub. No.: WO00/62669

PCT Pub. Date: Oct. 26, 2000

(30) Foreign Application Priority Data

Apr. 19, 1999 (IL) ........................... 129508

(51) Int. Cl.
*A61B 5/04* (2006.01)
*A61B 5/02* (2006.01)

(52) U.S. Cl. .............. 600/546; 600/506; 600/509; 600/382; 600/384

(58) Field of Classification Search ................ 600/546, 600/506, 509, 382, 384
See application file for complete search history.

(56) References Cited

U.S. PATENT DOCUMENTS

| | | | |
|---|---|---|---|
| 5,361,775 A | 11/1994 | Remes et al. | |
| 5,549,656 A * | 8/1996 | Reiss | 607/48 |
| 5,776,073 A | 7/1998 | Garfield et al. | |
| 5,795,304 A * | 8/1998 | Sun et al. | 600/546 |

FOREIGN PATENT DOCUMENTS

| | | |
|---|---|---|
| EP | 0 366 127 A | 5/1990 |
| EP | 0 366 127 A1 | 5/1990 |

(Continued)

OTHER PUBLICATIONS

"Electrogastrography: measurement, analysis and prospective applications" by J. Chen and R.W. McCallum; 2200 Medical & Biological Engineering & Computing; Jul. 29, 1991, No. 4.

(Continued)

*Primary Examiner*—Max Hindenburg
*Assistant Examiner*—Jeffrey G Hoekstra
(74) *Attorney, Agent, or Firm*—Birch, Stewart, Kolasch & Birch, LLP

(57) ABSTRACT

A system and method for determining smooth muscle motor activity in body organs. The system comprises electrodes for recording an analog signal in the subject's body, an analog to digital converter that converts the analog signal to a digital signal and a processor. Processing the digital signal includes obtaining power spectra of the digital signal, and identifying one or more frequency peaks in the power spectra. A peak in the power spectrum is identified within a frequency range in which an organ generates slow waves. The energy of the identified frequency peak is measured and an energy above a characteristic threshold is indicative of smooth muscle motor muscle motor activity in the respective organ.

36 Claims, 13 Drawing Sheets

FOREIGN PATENT DOCUMENTS

| | | |
|---|---|---|
| RU | 2023419 C1 | 11/1994 |
| RU | 2044513 C1 | 9/1995 |
| RU | 2054885 C1 | 2/1996 |
| RU | 2088147 C1 | 8/1997 |
| RU | 2095020 C1 | 11/1997 |
| SU | 1124919 A | 11/1984 |

OTHER PUBLICATIONS

Chen et al.: "Electrogastrography: Measurement, Analysis and Prospective Applications" vol. 29, No. 4, Jul. 1, 1991, pp. 339-350, XP000208760 ISSN: 0140-0118.

* cited by examiner

DETECTION OF SMOOTH MUSCLE MOTOR ACTIVITY

This application is the national phase under 35 U.S.C. § 371 of PCT International Application No. PCT/IL00/00215 which has an International filing date of Apr. 11, 2000, which designated the United States of America and was published in English.

FIELD OF THE INVENTION

The present invention is in the field of medical devices. More specifically, the invention relates to devices for examining smooth muscle organs.

BACKGROUND OF THE INVENTION

The major smooth muscle organs of the body include the gastrointestinal (GI) tract organs, the urinary bladder, and the uterus. The motor activity associated with these organs is essential in many physiological processes such as digestion, excretion and parturition. Many pathologies arising from impaired smooth muscle motor activity are known. In the GI tract, for example, smooth muscle dysfunction is a common pathology often making life for those suffering from it uncomfortable and painful.

The electrical activity of smooth muscle may consist of two components: slow waves and action potentials. Slow waves are periodic, spontaneously generated, low frequency signals. Characteristic frequency ranges of the slow wave of some GI tract organs are shown in Table 1. Slow waves propagate throughout the body and may be detected using electrodes disposed far from the wave source. Since the slow waves of the various smooth muscle organs have different characteristic frequency ranges, the slow waves generated by different organs can be resolved from the obtained signal by spectral analysis. No correlation exists between slow waves and motor activity. Thus, slow waves may be detected in the various GI tract organs during periods of motor activity as well as during periods of quiescence. Indeed, slow waves occur in the GI tract even in the absence of any motor activity such as in cases of gastro or intestinal paresis.

Smooth muscle contraction is always accompanied by a burst of action potentials and the generation rate of the action potentials per unit volume muscle tissue is proportional to the generated contractile force. An action potential burst, and hence contraction, can occur only on the crest of a slow wave, so that slow waves are involved in the timing of smooth muscle contraction. Slow waves also synchronize smooth muscle contraction, for example, along the GI tract. This gives rise to the migrating myoelectrical complex (MMEC) in which a region of muscle contractions migrates along the GI tract from the stomach to the ileum. Unlike slow waves, however, the propagation distance of an action potential is very short (several millimeters). Therefore, action potentials, and hence motor activity, are detected only with electrodes implanted in the wave source. In order to monitor action potentials along the entire GI tract, several electrodes implanted along the length of the GI tract must be used.

Russian Patents Nos. 2,088,147; 2,095,020; 2,054,885; 2,044,513; 2,623,419 and SU 1,124,919 disclose recording the electrical activity of the GI tract using cutaneous electrodes placed on body extremities. The signal is filtered to remove components not arising from the GI tract and a power spectrum of the filtered signal is obtained. Since the slow waves of the various GI tract organs (stomach, duodenum, jejunum, ileum) have non-overlapping, characteristic frequency ranges (Table 1), each peak in the power spectrum can be associated with (a different GI tract organ. These methods detect slow waves of the GI tract organs but not action potentials. Since it is the action potential burst and not the slow wave that is correlated with motor activity, these methods do not provide any information on GI tract motor activity. These methods, therefore, have not found much use in practice.

TABLE 1

Basic frequencies (Hz) of the slow waves of some gastrointestinal tract organs

| Organ | Human | Dog |
|---|---|---|
| Stomach | 0.05-0.08 | 0.04-0.09 |
| Duodenum | 0.19-0.21 | 0.29-0.35 |
| Jejunum | 0.165-0.19 | 0.25-0.29 |
| Ileum | 0.133-0.165 | 0.20-0.25 |

SUMMARY OF THE INVENTION

The present invention provides a method for detecting smooth muscle motor activity. The invention is based on the observation that the repolarization time of action potentials in smooth muscle cells is several seconds which is comparable to the period of the slow waves. It was further found that, in accordance with the invention, during motor activity, the form of the slow waves, and in particular their amplitude, is altered by the concomitant action potential burst. Moreover, it was also found that overlapping action potentials reinforce one another resulting in an amplification of the action potential effect on the slow waveform.

Thus, in accordance with the invention, an electrical signal comprising one or more slow waves generated by smooth muscle organs of the body is recorded. A power spectrum of the signal is obtained, for example, by a Fourier or Hartley transform of the signal. The area under a peak in the power spectrum is referred to herein as the energy of the peak and is denoted by E. In accordance with the invention, an action potential burst, and hence smooth muscle motor activity, in an organ, is detected as an increase in energy E of a spectral peak at the frequency of the slow wave generated by the organ above a predetermined threshold value for the organ.

Thus, in its first aspect, the invention provides a system for determining smooth muscle motor activity in one or more organs in a subject's body, the system comprising:
  (a) one or more electrodes recording at least one analog signal in the subject's body;
  (b) an analog to digital converter converting each of the at least one analog signal to a digital signal; and
  (c) a processor processing the one or more digital signals, wherein the processing comprises:
    (ca) obtaining a power spectrum of one or more of the at least one digital signal;
    (cb) identifying one or more frequency peaks in one or more of the one or more power spectra; and
    (cc) for each of the one or more organs in the subject's body,
      (cca) identifying a peak in an obtained power spectrum within a frequency range in which the organ generates slow waves;
      (ccb) measuring the energy, E, of the identified frequency peak in the obtained power spectrum; and
      (ccc) determining whether the measured energy E exceeds a predetermined threshold value, a measured energy E greater than the predetermined threshold being indicative of smooth muscle motor activity in the organ in the subject's body.

In its second aspect, the invention provides a method for determining smooth muscle motor activity in one or more organs in a subject's body, the method comprising:

(a) recording at least one analog signal in the subject's body;

(b) converting each of the at least one analog signal to a digital signal; and (c) processing the one or more digital signals, wherein the processing comprises:

(ca) obtaining a power spectrum of one or more of the at least one digital signal;

(cb) identifying one or more frequency peaks in one or more of the one or more power spectra; and (cc) for each of the one or more organs in the subject's body, (cca) identifying a peak in an obtained power spectrum within a frequency range in which the organ generates slow waves;

(ccb) measuring the energy, E, of the identified frequency peak in the obtained power spectrum; and (ccc) determining whether the measured energy E exceeds a predetermined threshold value, a measured area greater than the predetermined threshold being indicative of smooth muscle motor activity in the organ in the subjects body.

BRIEF DESCRIPTION OF THE DRAWINGS

In order to understand the invention and to see how it may be carried out in practice, a preferred embodiment will now be described, by way of non-limiting examples only, with reference to the accompanying drawings, in which.

DETAILED DESCRIPTION OF SPECIFIC EMBODIMENTS

Figure 1:
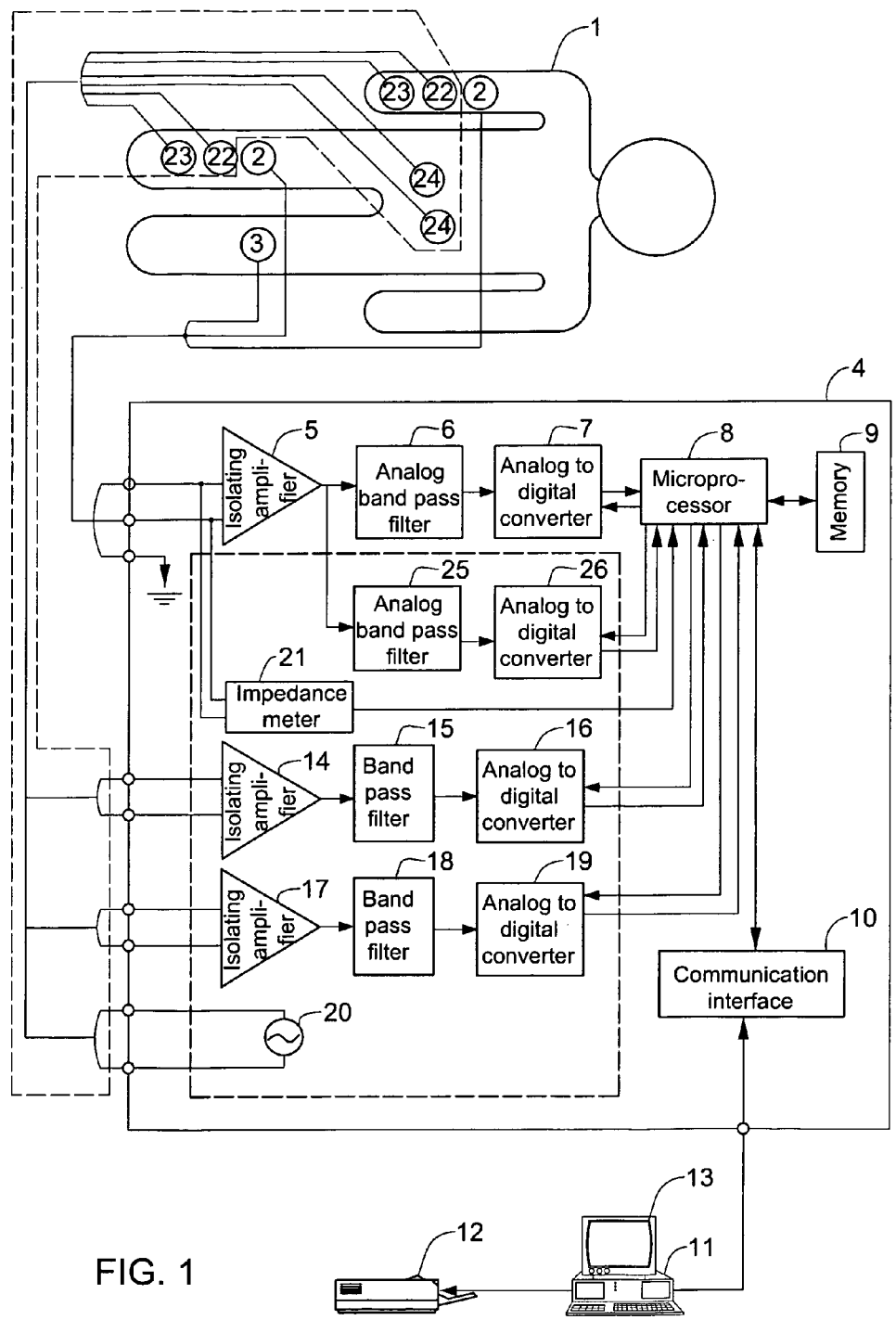
FIG. 1 shows a system for detecting smooth muscle activity in a body organ in accordance with an embodiment of the invention.

Reference is first made to FIG. 1 which shows a system for detecting smooth muscle activity in a body organ in accordance with an embodiment of the invention. The system comprises acquisition unit 4 and a host computer 11. Electrodes 2 and 3 are disposed on the subject 1. The electrodes may be cutaneous electrodes or implanted electrodes and may be disposed anywhere in or on the body of subject 1. The electrodes are preferably placed far from large blood vessels that might otherwise introduce extraneous components into the signal. In a preferred embodiment, cutaneous electrodes are disposed on the subject's limbs.

For example, as shown in FIG. 1, cutaneous recording electrodes 2 may be placed on the subject's right arm and above the right ankle and a reference electrode 3 may been placed above the left ankle. Electrodes known per se in the art may be used, e.g. Red Dot™ Ag—AgCl electrodes manufactured by 3M™.

The recording electrodes 2 are connected to the differential inputs of isolating amplifier 5 and the reference electrode 3 is connected to the ground. The amplified signal enters analog band pass filter 6. The filter 6 removes extraneous frequencies, for example, those originating from cardiovascular and/or respiratory signals. The filtered signal then enters analog to digital converter 7.

The digital signal enters microprocessor 8. The acquired signal may be stored in memory 9. Microprocessor 8 comprises digital band pass filters corresponding to the frequency ranges of the organs of interest. Microprocessor 8 is connected via communication interface 10 to host computer 11. The data obtained from acquisition unit 4 is stored on the host computer's hard disk. Host computer 11 produces a power spectrum, for example, by a fast Fourier transform (FFT) and/or a fast Hartley transform (FHT) of the signal. The signal and the results of the analysis may be stored on the host computer's hard disk, displayed on a screen 13, or printed out by a printer 12.

Recording electrodes 2 may also be connected to an impedance meter 21 for measuring the impedance between recording electrodes 2. The impedance measured by impedance meter 21 enters microprocessor 8. The measured impedance may be used as an indication of the quality of the contact of the electrodes 2 to the body of subject 1.

The signal produced by amplifier 5 may also enter analog band pass filter 25 which isolates cardiovascular and/or respiratory signals. This filtered signal enters analog to digital converter 26 and this digital signal enters microprocessor 8. Since cardiovascular and respiratory signals are well defined periodic signals having frequencies significantly higher than those of the smooth muscle organs, the signal produced by converter 26 can be used for continuously monitoring the quality of the contact of the electrodes with the subject's body.

The registration of the signal may be accomplished by multiple electrodes in which case additional recording electrodes 22 are disposed close to recording electrodes 2. The signals recorded by electrodes 22 are connected to the differential inputs of isolating amplifier 14. The amplified signal enters analog band pass filter 15 which removes extraneous frequencies. This filtered signal then enters analog to digital converter 16, and the digital signal enters microprocessor 8. Comparison of the signal recorded by electrodes 2 with that recorded by electrodes 22 allows evaluation of the galvanic skin potential and common mode noise, which may then be eliminated from the signal in the subsequent processing.

The system may also include a signal generator 20 for producing a low amplitude periodic "pilot signal" for identification of noise. The pilot signal has a frequency within the frequency range of filter 6 and preferably close to but different from any frequency of interest. The pilot signal may be induced via registration electrodes 2 or 3, or via one or more dedicated electrodes 23. Singular (non-periodic) noise in the recorded signal at the pilot signal frequency is easily identified. Since singular noise has a wide frequency spectrum it affects the recorded signal at all frequencies similarly. Use of a pilot signal thus allows identification and elimination of singular noise in the recorded signal at all frequencies.

The device and method of the invention are demonstrated in the following non-limiting examples.

Example 1

Validation of the Method and System of the Invention in Dogs

Figure 2:
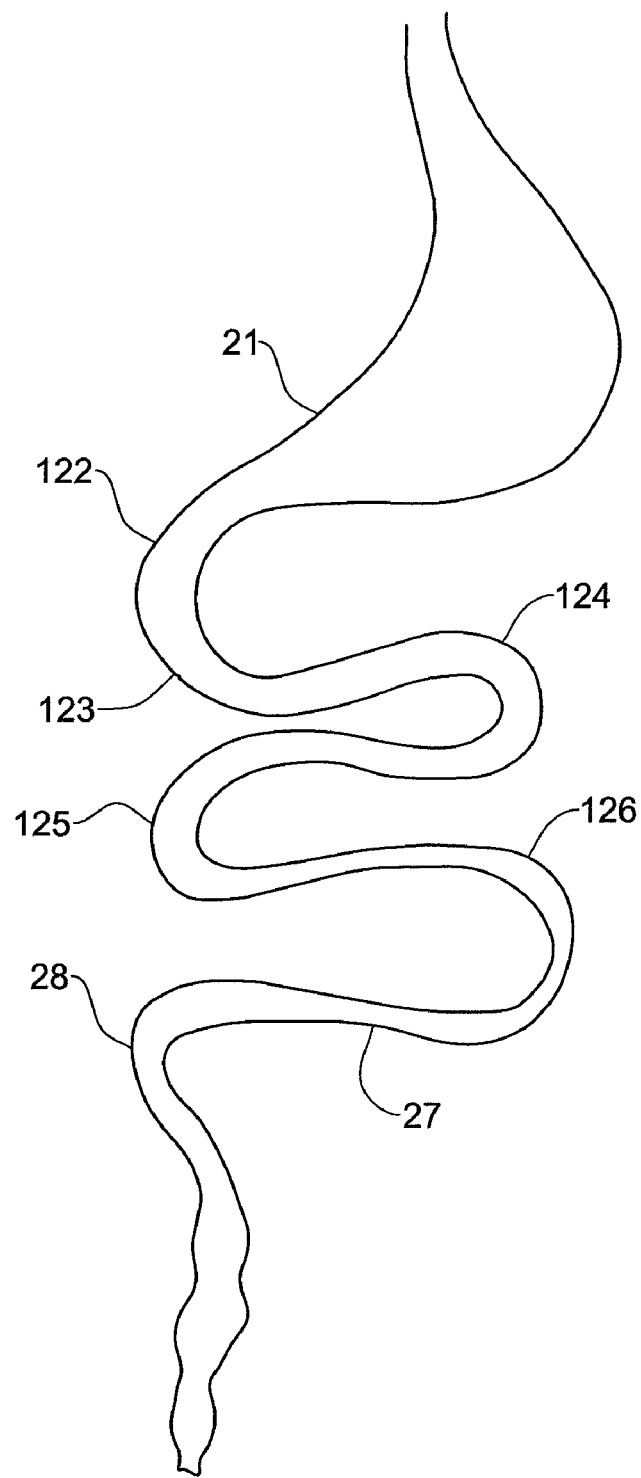
FIG. 2 shows the locations of electrodes implanted in the GI tract of dogs.

The method of the invention was validated in 6 healthy dogs by comparing the signal recorded by cutaneous electrodes in accordance with the invention with signals recorded simultaneously by electrodes implanted in various locations in the GI tract of the dogs. Cutaneous Ag—AgCl electrodes (Red Dot™, 3M™ Company, Canada) were used. A recording electrode was disposed on each one of the right limbs and a reference electrode was disposed on the left hind limb of each dog. The electrodes had a noise level of less than 1 mV below 0.04 Hz. In addition, 8 bipolar platinum electrodes (0.2 mm diameter, 2 mm separation) were implanted in the GI tract of the dogs. The locations of the implanted electrodes were as indicated in FIG. 2. Location 21 is the stomach antrum, 122 is the proximal part of the duodenum, 123 is the distal part of duodenum, 124, 125, 126, and 27 are different parts of jejunum, and 28 is the ileum.

The amplifier used had a symmetrical input with impedance of over 100 KOhm, and a common mode rejection ratio of at least 60 db to reduce common mode noise in the signal. The band pass range of the amplifier was 0.05-0.3 Hz. The output of the amplifier was digitized with an at least 12 bit resolution and a conversion frequency of 5 Hz. The host computer comprised a personal computer having an Intel Pentium processor.

A time window of 3-5 min was used with 2 min time steps. This time window includes at least 10 periods of the slowest GI tract slow wave analyzed (that of the stomach) and significantly exceeds the period of the ultra-low frequency noise, for instance that of the colon. The ultra-low frequency noise is thus a periodic component, and not a drift in the signal, and is cancelled out over the long time window. During this time window, the signals of the GI tract organs are quasi-steady so that methods of spectral analysis may be used to reveal them, while the ultra-low frequencies are filtered out.

Averaging the signal over each time window was performed by the host computer to identify trends in the signal due to components having periods comparable to or greater than the time window. The time average of components having periods significantly shorter than the time window is essentially 0 and are therefore eliminated in the averaging. The time average of the signal between windows was obtained by interpolation to produce a continuous trend curve that was subtracted from the signal.

A Fourier transform of the signal was then performed by the host computer. The energy E of each peak at frequencies shown in Table 1 was calculated and used as a measure of the amplitude of the corresponding slow wave.

Figure 3A:
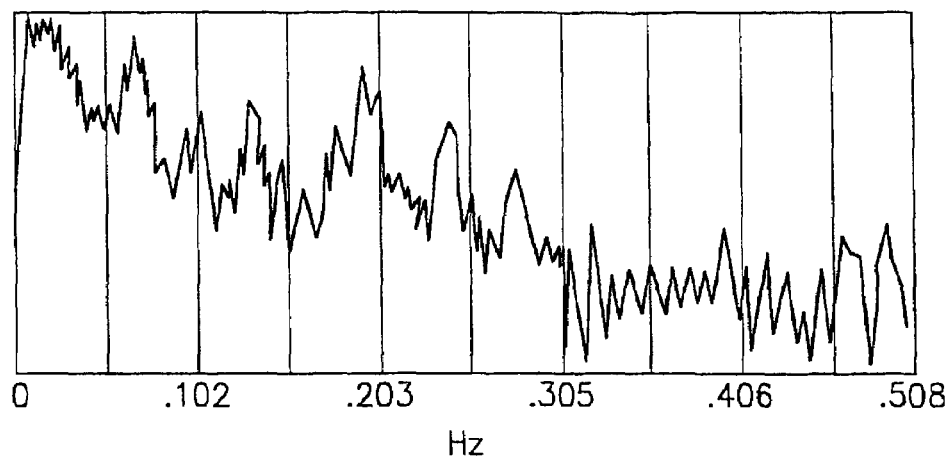
FIG. 3a shows the sum of the power spectra of 8 signals recorded by electrodes implanted in the GI tract organs of dogs.
Figure 3B:
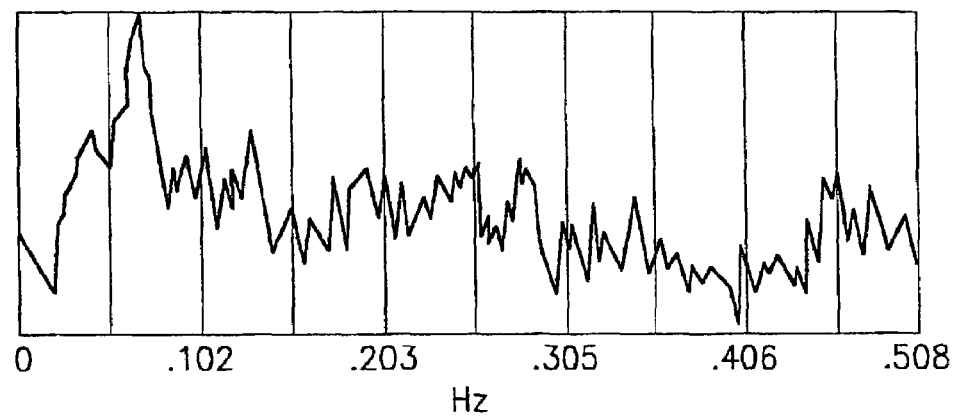
FIG. 3b shows the power spectrum of a signal recorded by cutaneous electrodes in the dogs.
Figure 3C:
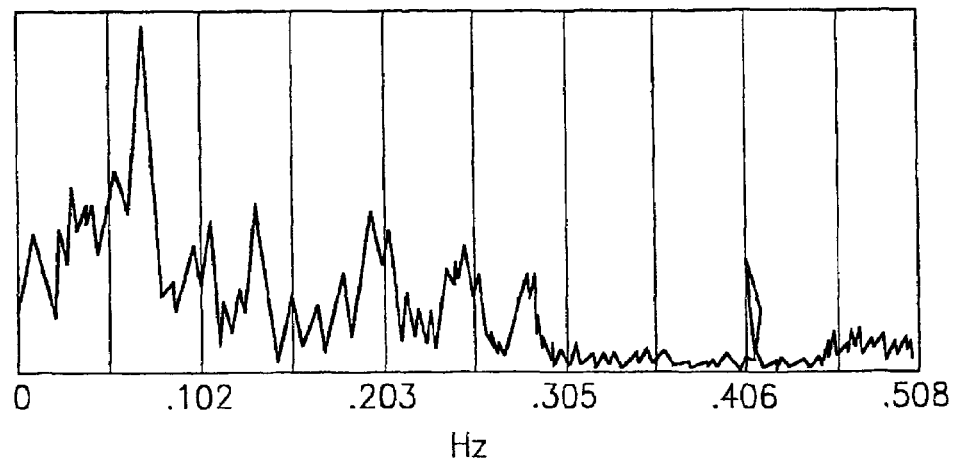
FIG. 3c is the cross correlation of the power spectra of FIGS. 3 a and b.

FIG. 3 shows a comparison of the sum of the power spectra of the signals recorded by the 8 implanted electrodes (FIG. 3a) with the signal recorded simultaneously by the cutaneous electrodes (FIG. 3b). FIG. 3c shows the cross correlation of the power spectra shown in FIGS. 3a and 3b, demonstrating the strong correlation between the two spectra. The locations of the peaks in the two spectra were found to be identical in 99.4% of all recordings.

Figure 4:
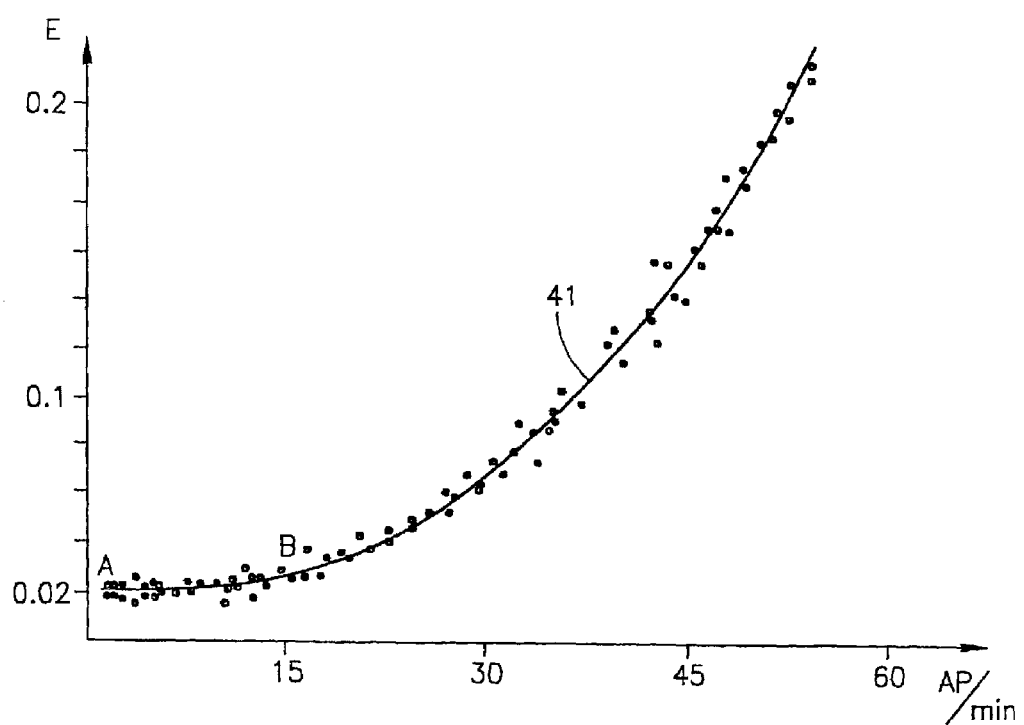
FIG. 4 shows the correlation between E and the generation rate of action potentials.

The energy E and the generation rate of action potentials (AP per minute) were monitored simultaneously in each dog for two hours. During the two hours, the dogs were treated with prozerin (0.2-0.3 mg/Kg body weight), acetylcholine (1.0-1.5 mg/Kg body weight), or atropine sulfate (0.15 mg/Kg body weight) to stimulate or inhibit smooth muscle motility. FIG. 4 shows AP as a function of E in the jejunum. Each point in FIG. 4 represents a pair of simultaneous E and AP measurements obtained on the jejunum under one of the various treatments used. All of the data points are adequately described by a single smooth curve 41 irrespective of the individual dog, or the treatment administered to the dog when the measurements were made. In the range of the lowest values of E measured (<0.03), the action potential generation rate is also low (about 1-15 per min). These are sporadic action potentials not comprising an action potential burst. Thus, in the points along the portion of curve 41 between points A and B, no significant muscle contraction is occurring. As the measured value of E rises above 0.03, the generation rate of action potentials increases so as to form action potential bursts. Therefore, a burst in action potentials, and hence muscle contraction, in the jejunum occurs only when the energy E of the jejunum peak in the power spectrum exceeds a threshold of about 0.03.

Example 2

Recording the Migrating Myoelectrical Complex in Dogs

Figure 5A:
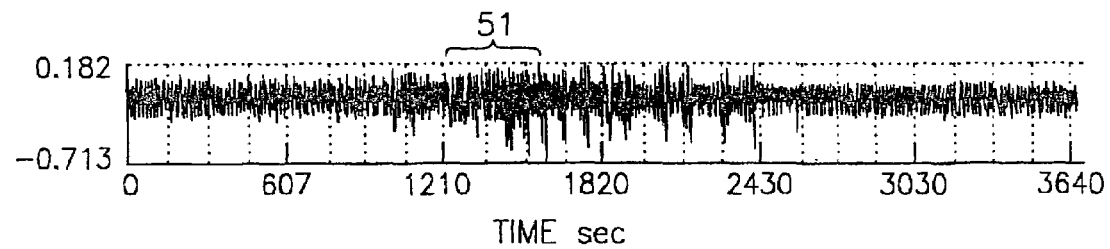
FIG. 5 shows the migrating myoelectrical complex in dogs.
Figure 5B:
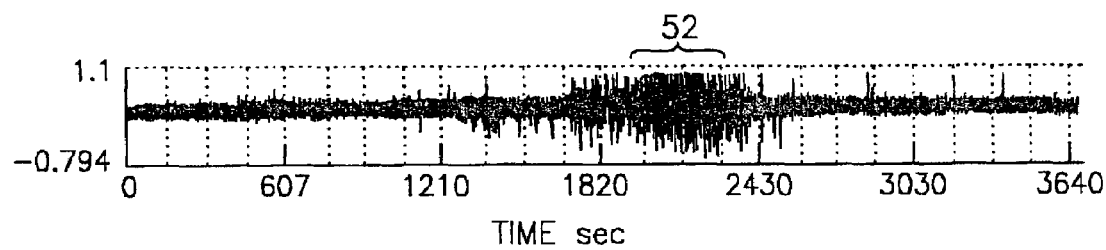
Figure 5C:
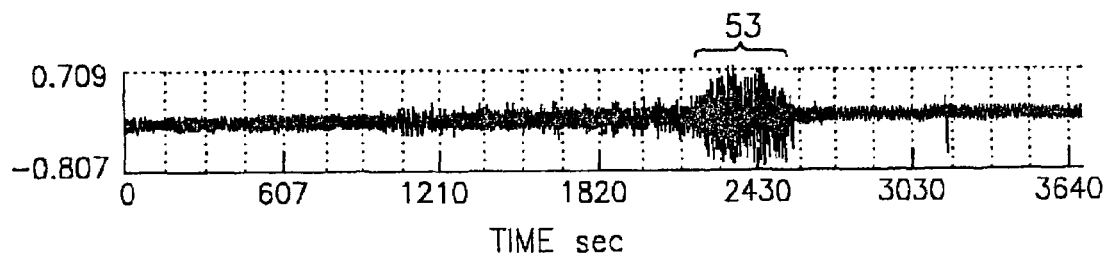
Figure 5D:
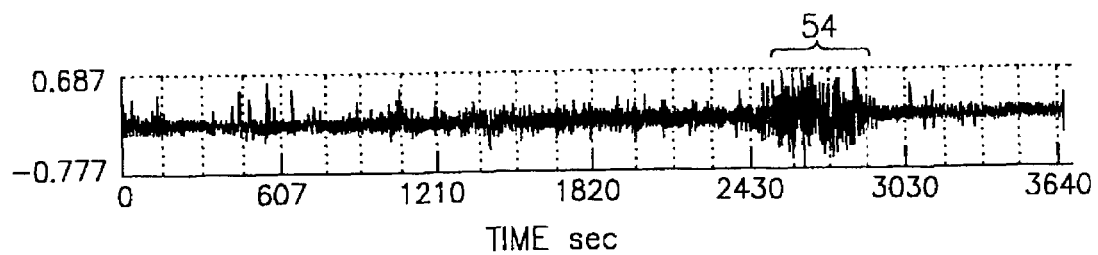
Figure 5E:
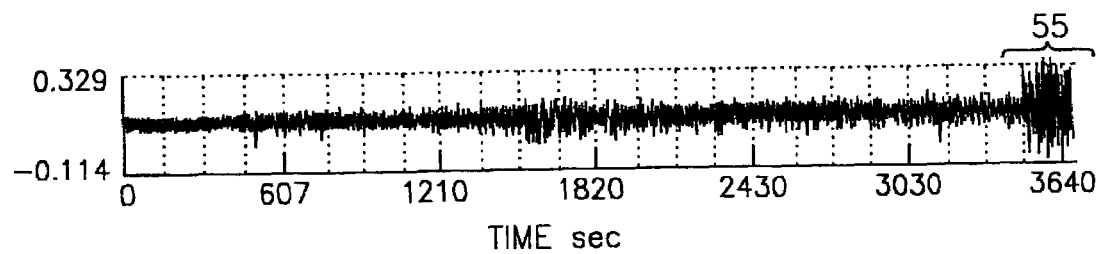
Figure 5F:
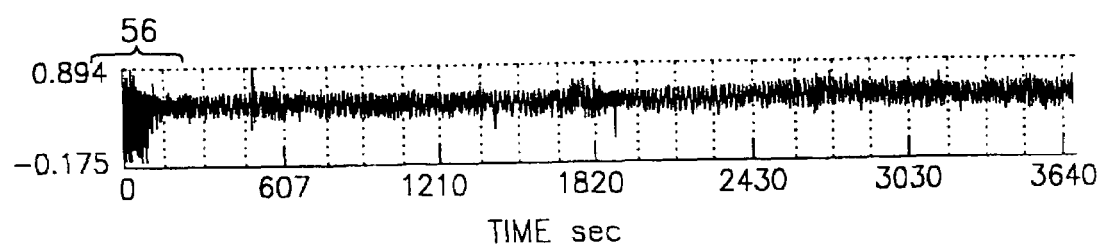
Figure 5G:
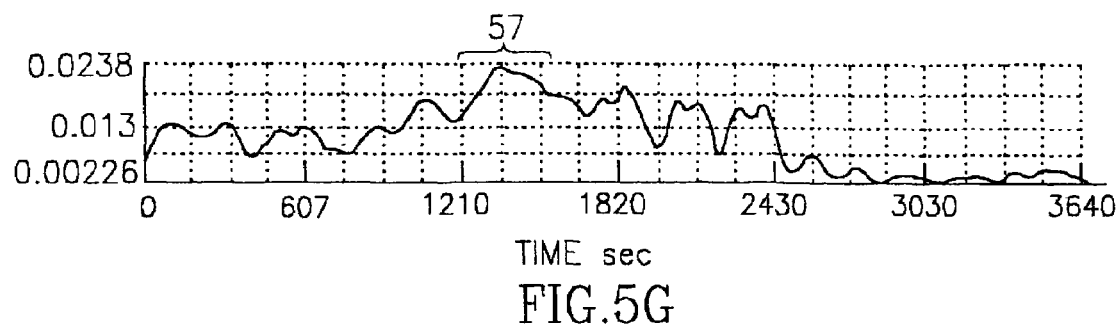
Figure 5H:
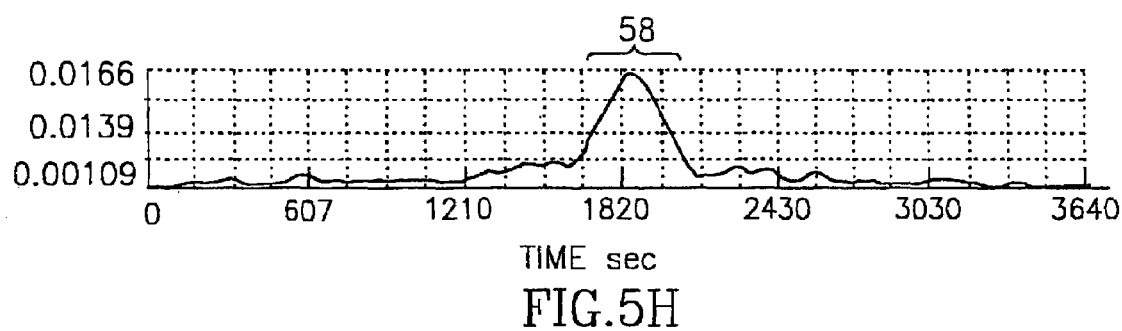
Figure 5I:
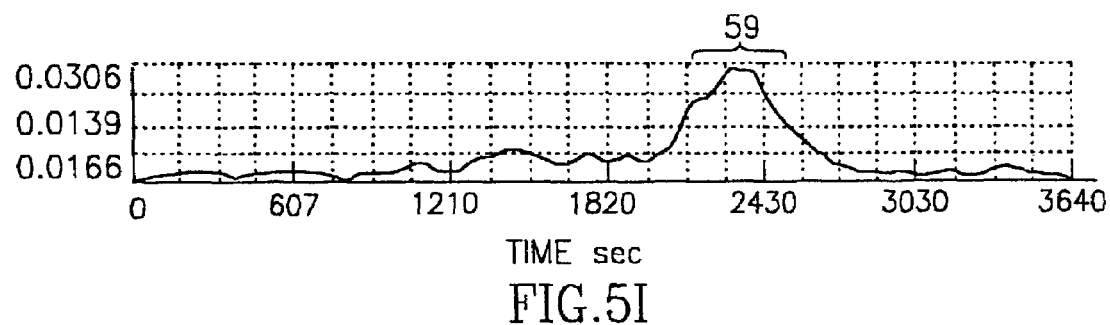
Figure 5J:
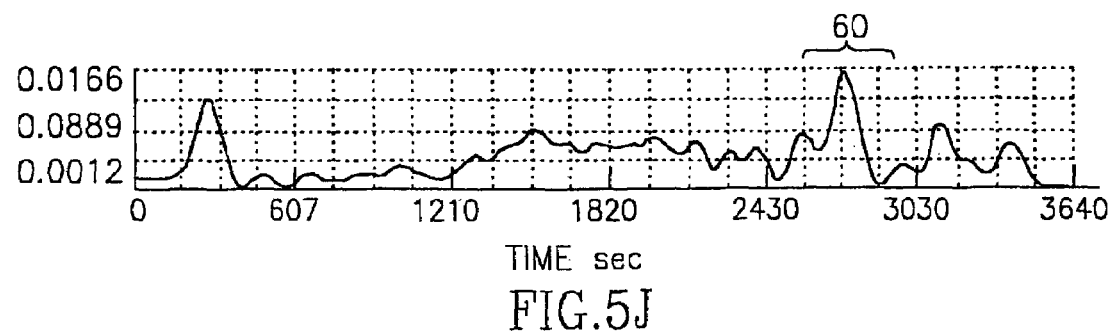

The system and method of Example 1 were used to detect the migrating myoelctrical complex (MMEC) in dogs. FIG. 5, panels a to f, show the action potentials recorded simultaneously by electrodes implanted in the GI tract of a dog over time. Bursts of action potentials corresponding to muscle contraction are indicated in FIG. 5, panels a-f by brackets 51 to 56, respectively. Transient muscle contraction was detected in the stomach (bracket 51 in FIG. 5a). The region of contraction then migrated to the duodenum (bracket 52 in FIG. 5b), then along the jejunum (brackets 53, 54, 55 in FIGS. 5c-e). In the ileum, bracket 56 indicates the muscle contraction of the previous wave (FIG. 5f). FIG. 5, panels g-j, show simultaneous measurements of the energy E obtained by processing the signals recorded by the cutaneous electrodes. In accordance with the invention, elevated E indicates increased muscle contraction in the organ, and this is indicated in FIG. 5 panels g to j by brackets 57 to 60, respectively. Paralleling the results obtained with the implanted electrodes, peaks in E were observed in the stomach (bracket 57 in FIG. 5g), then in the duodenum (bracket 58 in FIG. 5h), an in the jejunum (bracket 59 in FIG. 5i.), and in the ileum (bracket 60 in FIG. 5j).

Example 3

Validation of the Method and System of the Invention in Human Subjects

Figure 6A:
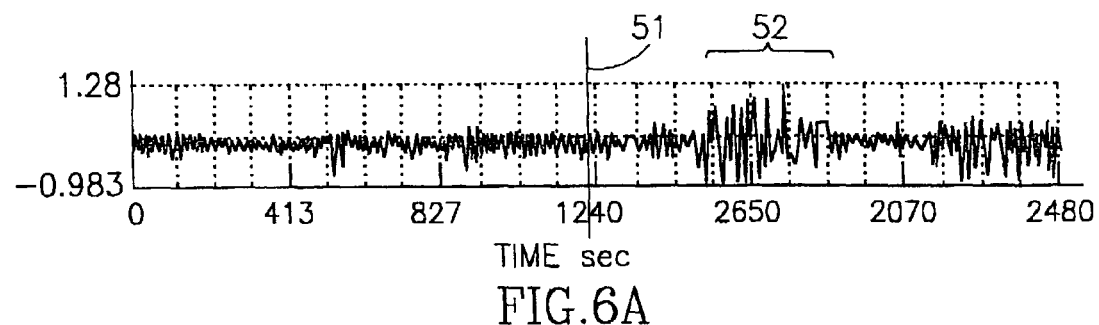
FIG. 6 is the correlation between the signal recorded by cutaneous electrodes (FIG. 6a) and the pressure wave recorded by an open catheter in the jejunum (FIG. 6b) in a human subject.
Figure 6B:
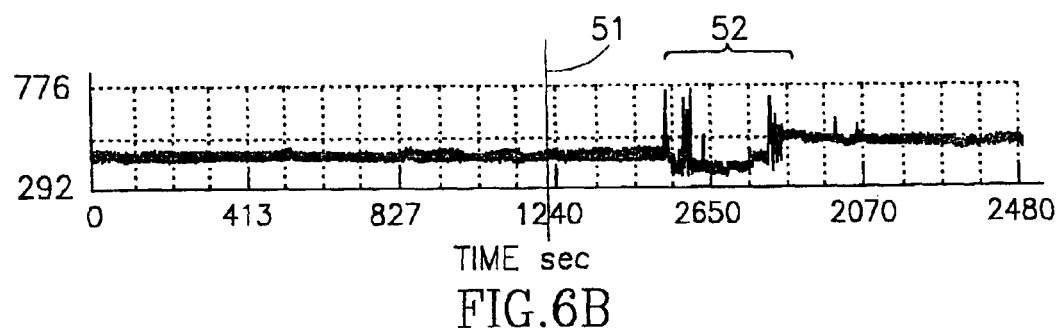

Cutaneous electrodes were disposed on human subjects as shown in FIG. 1. The cutaneous electrodes used as well as the processing of the signal recorded by these electrodes were as described in Example 1. Evaluation of GI tract motor function by measurement of bowel pressure was simultaneously performed using an open catheter inserted into the jejunum during surgery. FIG. 6a shows the total signal recorded by the cutaneous electrodes over a period of about 40 min, and FIG. 6b shows the simultaneous pressure measurements recorded by the catheter. At the time indicated by the vertical line 51, 0.2 mg/kg body weight prozerin was administered to the subject. This treatment induced a transient increase in the amplitude of the slow waves during the time period 52. Simultaneously, pressure waves indicative of smooth muscle contraction were detected by the catheter (FIG. 6b).

Figure 7A:
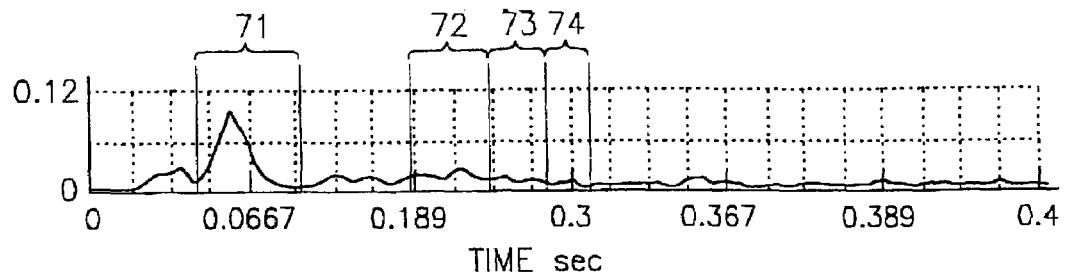
FIG. 7 is power spectra of the slow waves in a human subject obtained at various times (a) 0 min; (b) 10 min; (c) 35 min; (d) 45 min; and (e) 50 min.
Figure 7B:
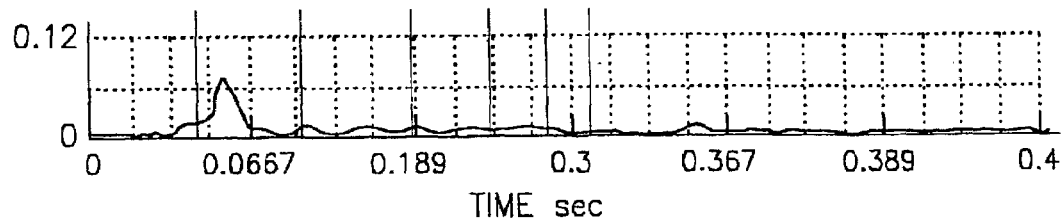
Figure 7C:
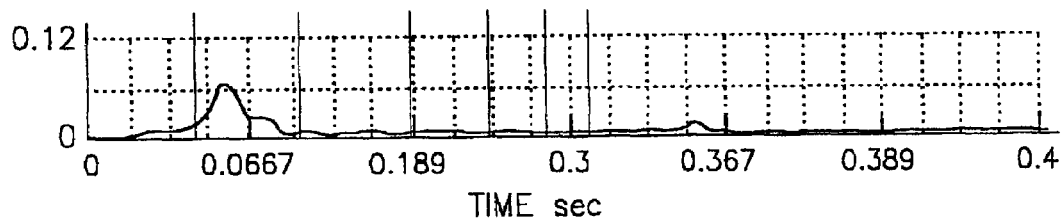
Figure 7D:
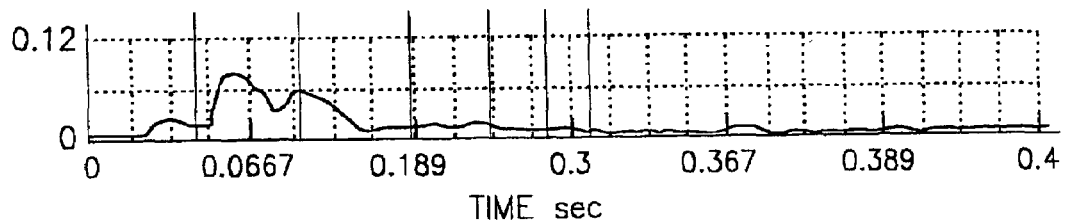
Figure 7E:
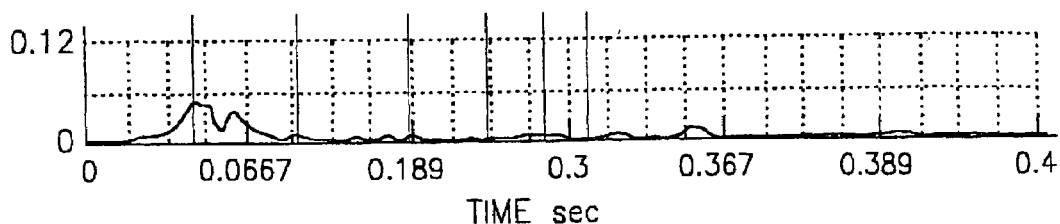
Figure 8A:
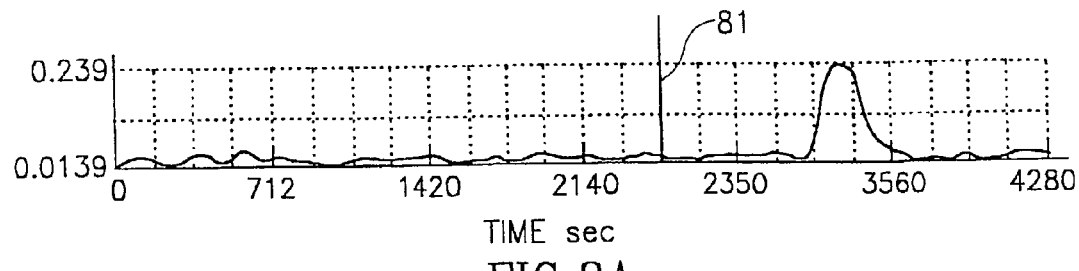
FIG. 8 shows E as a function of time in the (a) stomach, (b) duodenum, (c) jejunum, and (d) ileum of a human subject.
Figure 8B:
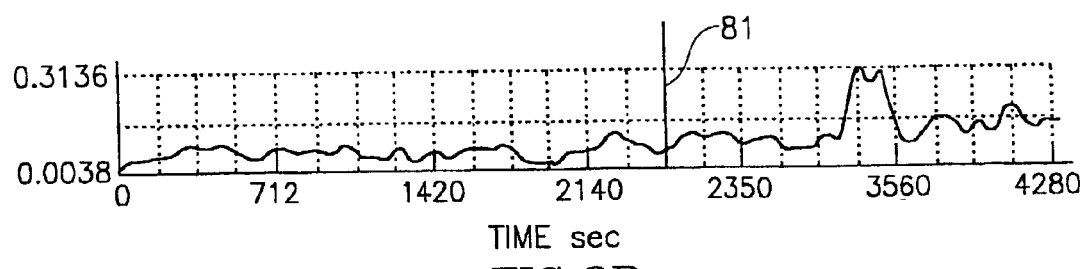
Figure 8C:
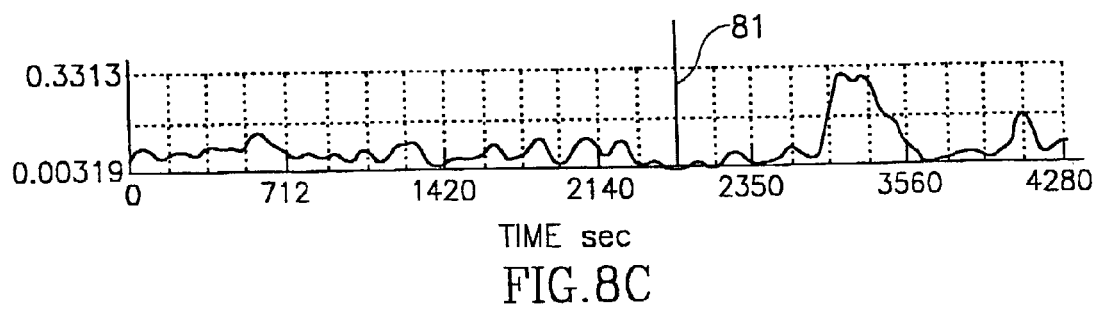
Figure 8D:
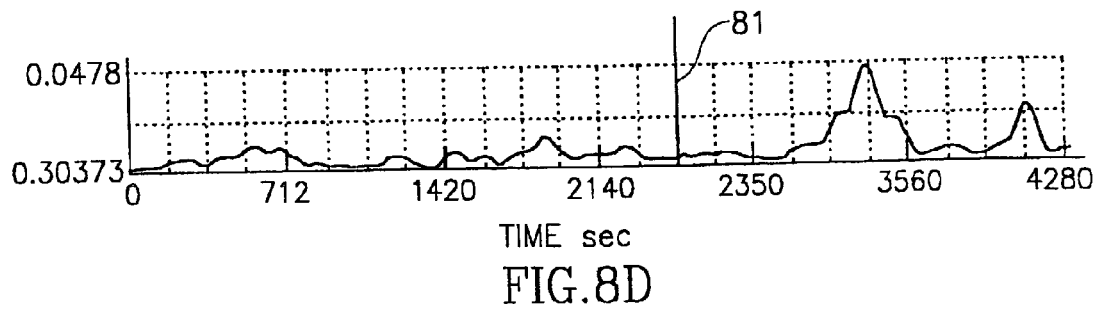

Power spectra of the signal from the electrodes are shown in FIG. 7 at various times (FIG. 7a, 0 min; b 10 min; c 35 min; d 45 min. e 50 min. The frequency intervals in the power spectrum indicated by brackets 71, 72, 73, and 74, are the frequency ranges of the slow wave of the stomach, ileum, jejunum and duodenum, respectively. At time 40 min, 0.2 mg/kg body weight prozerin was administered to the subject to transiently stimulate smooth muscle activity. A significant increase in the measured energy E was observed 5 min later in each organ (FIG. 7d), which was followed by a decrease in E (FIG. 7e). FIG. 8 shows the time dependencies of the energy E of the peak corresponding to the signal generated by the stomach (FIG. 8a), the duodenum (FIG. 8b), the jejunum (FIG. 8c) and the ileum (FIG. 8d) of the subject. Vertical line 81 indicates the time at which 0.2 mg/1 µg body weight prozerin was administered to the subject. This lead to a transient increase in E for each organ indicating muscle contraction in the organs.

Example 4

Diagnosis of Reverse Peristaltic Syndrome in a Human Subject

Figure 9A:
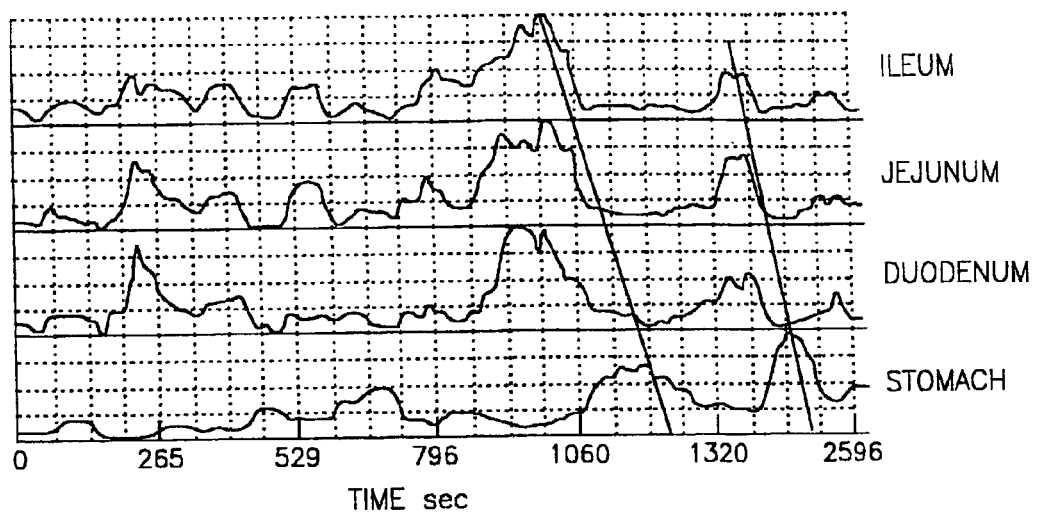
FIG. 9 shows the time dependence of E in the stomach, duodenum, jejunum and ileum of a patient with reverse-peristaltic syndrome undergoing cold therapy.
Figure 9B:
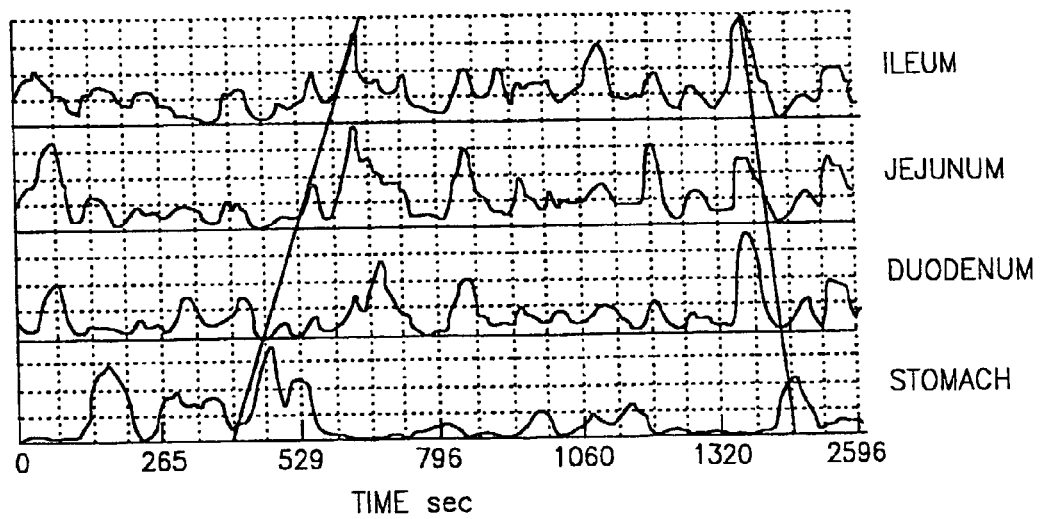
Figure 9C:
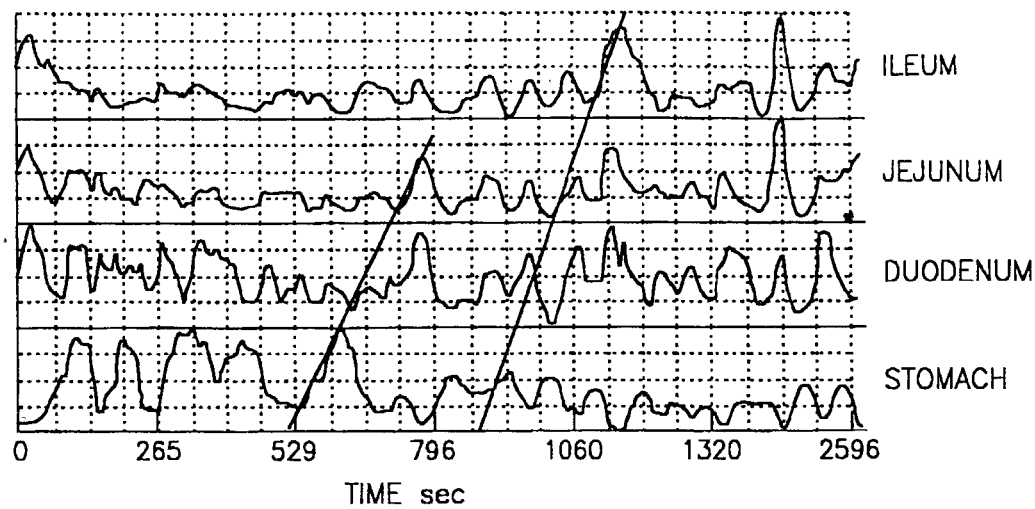
Figure 9D:
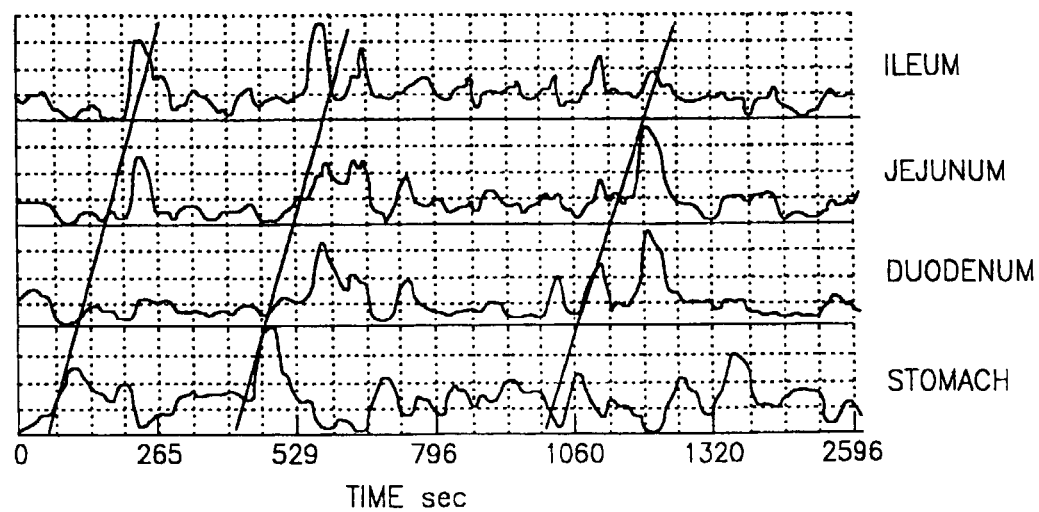

In the disorder known as reverse peristaltic syndrome, a region of increased electrical activity regresses from the ileum to the stomach, i.e. in the reverse direction to that of the migrating myoelectric complex (MMEC). The system and method of the invention were used for diagnosing reverse peristaltic syndrome in a human subject. In accordance with the invention, elevated E in a GI tract organ indicates smooth muscle contraction in the organ. FIG. 9 shows the time dependence of E in GI tract organs of the subject. In each panel in FIG. 9, straight lines join peaks of elevated E. A negative slope of the line as seen in FIG. 9a, for example, indicates a wave of contraction starting in the ileum and regressing through the jejunum and duodenum to the stomach, which is characteristic of reverse peristaltic syndrome. The subject was then treated by cold therapy consisting of daily anal cold treatments of 4-8° C. lasting 15 min. This treatment resulted in a gradual reversal of the peristaltic wave to the normal direction as indicated by the lines of positive slope in FIGS. 9b-d.

Example 5

Use of a Pilot Signal for Identifying and Eliminating Singular Noise

Figure 10A:
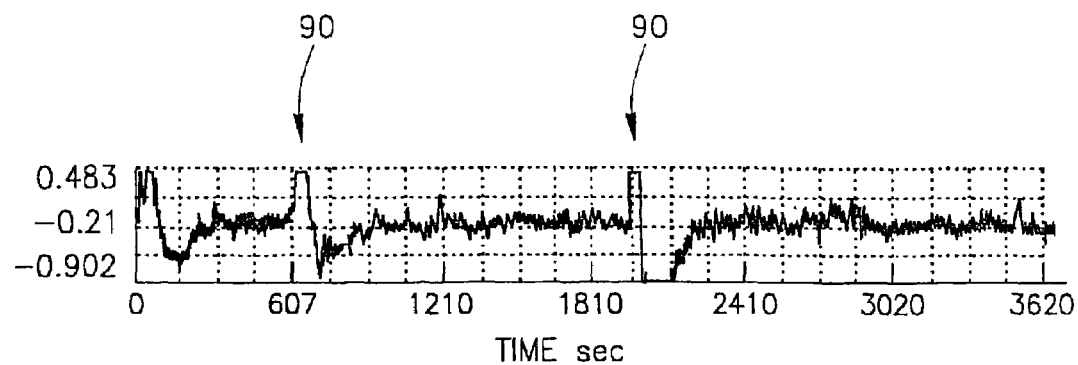
FIG. 10 shows use of a pilot signal for the identification of singular noise.

FIG. 10a shows a signal recorded with cutaneous electrodes using the system of Example 1. Examples of suspected singular noise are indicated by arrows 90.

Figure 10B:
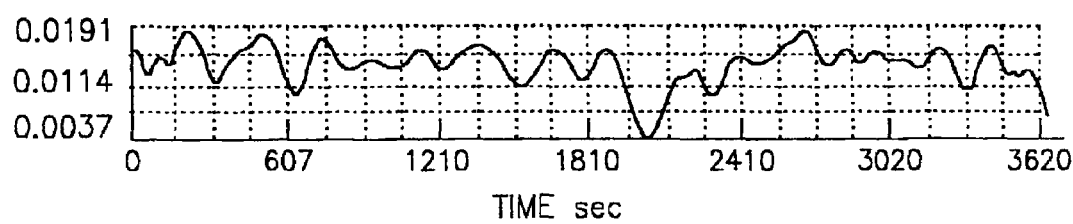
Figure 10C:
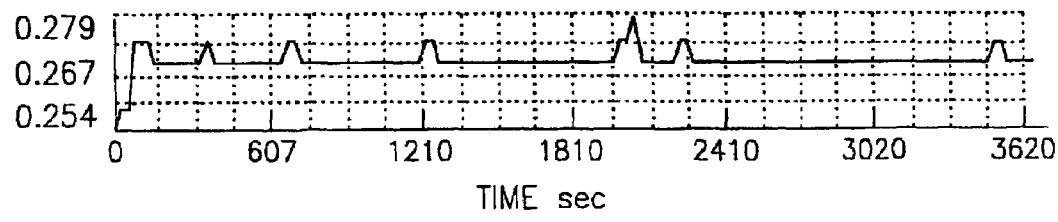

Singular noise may arise, for example, by the contraction of skeletal muscle near an electrode. A pilot signal generator was used as indicated in FIG. 1 to introduce a 0.27 Hz sine wave pilot signal. The signal recorded by the cutaneous electrodes after being passed through a narrow band pass filter at this frequency is shown in FIG. 10b. The Fourier transform of the filtered signal was obtained, and the location of the peak in the transform as a function of time is shown in FIG. 10c. Peaks in FIG. 10c indicate singular noise in the signal of FIG. 10a. The singular noise in FIG. 10a can then be eliminated by methods known in the art. For example, an interval in the signal of FIG. 10a containing singular noise may be replaced with a substitute signal obtained as the average of the signal in intervals of the same length immediately before and immediately after the interval containing the noise.

The invention claimed is:

1. A system for detecting action potentials of smooth muscle motor activity in two or more digest tract organs in a subject's body, the system comprising:
   (a) one or more cutaneous electrodes recording at least one analog signal in the subject's body, the electrodes being attached to the subject's limbs;
   (b) an analog to digital converter converting each of the at least one analog signal to a digital signal; and
   (c) a programmable processor processing the one or more digital signals and programmed for:
      (ca) obtaining a power spectrum of one or more of the at least one digital signal;
      (cb) identifying two or more frequency peaks in one or more of the one or more power spectra, the frequency peaks corresponding to respective organs of said two or more digestive tract organs; and
      (cc) for each of the two or more organs in the subject's body,
      (cca) identifying a peak for the respective organ in the obtained power spectrum within a frequency range in which the respective organ generates slow waves;
      (ccb) determining an area under the identified frequency peak in the obtained power spectrum as an energy, E; and
      (ccc) determining whether the energy E exceeds a predetermined threshold value, an energy E greater than the predetermined threshold being indicative of action potential of smooth muscle motor activity in the respective organ in the subject's body.

2. The system according to claim 1 wherein the electrodes are multiple electrodes.

3. The system according to claim 2 wherein the processing further comprises eliminating the contribution of the galvanic skin potential from the signal.

4. The system according to claim 2 wherein the processing further comprises eliminating the contribution of common mode noise from the signal.

5. The system according to claim 1, further comprising a filtering an analog signal recorded by the one or more electrodes.

6. The system according to claim 1, further comprising an impedance meter measuring the impedance between one or more pairs of electrodes so as to provide one or more impedance measurements.

7. The system according to claim 6 wherein the processing further comprises evaluating the quality of the contact of the electrodes to the subject's body from the one or more impedance measurements.

8. The system according to claim 1, further comprising a filter filtering an analog signal recorded by the one or more electrodes so as to obtain a cardiovascular or respiratory signal.

9. The system according to claim 8 wherein the processing further comprises evaluating the quality of the contact of the electrodes with the subject's body based on the cardiovascular or respiratory signal.

10. The system according to claim 1, wherein the processing further comprises eliminating trends in the signal.

11. The system according to claim 1, wherein the two or more organs are organs of the gastrointestinal tract.

12. The system according to claim 11 wherein the two or more organs are selected from the list comprising:
   (One) stomach;
   (Two) duodenum;
   (Three) jejunum; and
   (Four) ileum.

13. The system according to claim 1, further comprising digital filters discriminating one or more components in a digital signal specific to at least one of the organs.

14. The system according to claim 1, further comprising
   (a) a signal generator generating a periodic pilot signal at a pilot signal frequency;
   (b) one or more electrodes introducing the pilot signal into the subject's body;
   (c) detecting noise in an recorded signal at the pilot signal frequency;
   (d) removing the detected noise from all frequencies of the recorded signal.

15. A method for detecting action potentials of smooth muscle motor activity in or more digestive tract organs in a subject's body, the method comprising:
   (a) recording at least one analog signal in the subject's body with one or more cutaneous electrodes placed on the subjects limbs;
   (b) converting each of the at least one analog signal to a digital signal; and
   (c) processing the one or more digital signals, wherein the processing comprises:
      (ca) obtaining a power spectrum of one or more of the at least one digital signal;
      (cb) identifying two or more frequency peaks in one or more of the one or more power spectra, the frequency peaks corresponding to respective organs of said two or more digestive tract organs; and
      (cc) for each of the two or more organs in the subject's body,
         (cca) identifying a peak for the respective organ in the obtained power spectrum within a frequency range in which the respective organ generates slow waves;
         (ccb) determining an area under the identified frequency peak in the obtained power spectrum as an energy, E; and
         (ccc) determining whether the energy E exceeds a predetermined threshold value, an area greater than the predetermined threshold being indicative of action potential of smooth muscle motor activity in the respective organ in the subjects body.

16. The method according to claim 15 wherein the one or more analog signals are recorded using multiple electrodes.

17. The method according to claim 16 wherein the processing further comprises eliminating the contribution of the galvanic skin potential from the signal.

18. The method according to claim 16, wherein the processing further comprises eliminating the contribution of common mode noise from the signal.

19. The method according to claim 1 further comprising eliminating trends in the signal.

20. The method according to claim 15 wherein the two or more organs are organs of the gastrointestinal tract.

21. The method according to claim 20 wherein the two or more organs are selected from the list comprising:
   (e) stomach;
   (f) duodenum;
   (g) jejunum; and
   (h) ileum.

22. The method according to claim 15 further comprising filtering an analog signal recorded by the one or more electrodes.

23. The method according to claim 15 further comprising measuring the impedance between one or more pairs of electrodes so as to provide one or more impedance measurements.

24. The method according to claim 23 wherein the processing further comprises evaluating the quality of the contact of the electrodes to the subject's body based on the impedance measurements.

25. The method according to claim 15, further comprising filtering an analog signal recorded by the one or more electrodes so as to obtain a cardiovascular or respiratory signal.

26. The method according to claim 25 wherein the processing further comprises evaluating the quality of the contact of the electrodes with the subject's body based on the cardiovascular or respiratory signal.

27. The method according to claim 15, further comprising digital filters discriminating one or more components in a digital signal specific to at least one of the organs.

28. The method according to claim 15, further comprising
   (a) generating a periodic pilot signal at a pilot signal frequency
   (b) introducing the pilot signal into the subject's body;
   (c) detecting noise in an recorded signal at the pilot signal frequency;
   (d) removing the detected noise from all frequencies of the recorded signal.

29. The system according to claim 1 for use in determining smooth muscle motor activity in one or more organs in a subject's body.

30. The system according to claim 1 for obtaining a migrating myoelectrical complex in a subject's body.

31. The system according to claim 1 for use in the diagnosis of reverse peristaltic syndrome in a subject.

32. The method according to claim 15 for use in determining smooth muscle motor activity in one or more organs in a subject's body.

33. The method according to claim 15 for use in obtaining a migrating myoelectrical complex in a subject.

34. The method according to claim 15 for use in the diagnosis of reverse peristaltic syndrome in a subject.

35. A computer program comprising computer program code means for performing step (c) of claim 15 when said program is run on a computer.

36. A computer program as claimed in claim 35 embodied on a computer readable medium.

* * * * *